Figure 1:
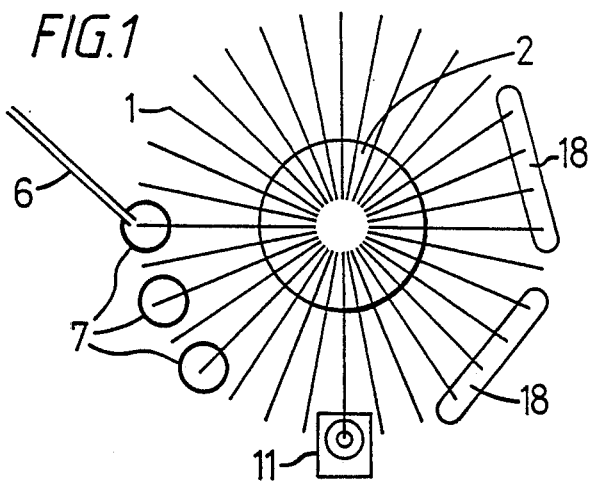

United States Patent [19]

Crighton et al.

[11] Patent Number: 4,820,044

[45] Date of Patent: Apr. 11, 1989

[54] TRANSPORT DETECTOR SYSTEM

[75] Inventors: James S. Crighton, Farnborough; David J. Malcolme-Lawes, Buckhurst Hill, both of England

[73] Assignee: The British Petroleum Company p.l.c., London, England

[21] Appl. No.: 119,575

[22] Filed: Nov. 12, 1987

[30] Foreign Application Priority Data

Nov. 15, 1986 [GB] United Kingdom ............... 8627362
Jul. 11, 1987 [GB] United Kingdom ............... 8716384

[51] Int. Cl.[4] ............... G01N 21/72; G01N 30/68; G01N 30/74; G01N 30/82
[52] U.S. Cl. ............... 356/315; 356/36; 356/72; 356/417; 356/244; 73/61.1 C; 210/198.2; 422/54; 422/64; 422/70; 436/154; 436/171
[58] Field of Search ............... 356/36, 38, 72, 300, 356/311, 315, 316, 417, 256, 244, 246; 250/288, 288 A; 73/23.1, 61.1 C; 210/198.2; 422/54, 63, 64, 70; 436/153, 154, 171

[56] References Cited

U.S. PATENT DOCUMENTS

| | | | |
|---|---|---|---|
| 3,376,694 | 4/1968 | Owens II, et al. | 73/23.1 |
| 3,744,973 | 7/1973 | Dubsky | 422/54 |
| 3,788,479 | 1/1974 | Szakasits | 73/23.1 |
| 4,215,090 | 7/1980 | Dixon | 422/54 |
| 4,271,022 | 6/1981 | Dixon et al. | 210/198.2 |
| 4,562,044 | 12/1985 | Bohl | 422/64 |

FOREIGN PATENT DOCUMENTS

| | | | |
|---|---|---|---|
| 136610 | 4/1985 | European Pat. Off. | 250/288 |
| 2424985 | 12/1975 | Fed. Rep. of Germany | 73/61.1 C |

*Primary Examiner*—F. L. Evans
*Attorney, Agent, or Firm*—Morgan & Finnegan

[57] ABSTRACT

A transport detector system comprises
(a) a liquid delivery tube,
(b) a plurality of moveable spokes, the spokes being positioned to pass in sequence under the delivery tube, the spokes being constructed from a refractory inorganic material of low thermal conductivity,
(c) one or more evaporators, positioned so that the spokes pass sequentially through it or them after liquid has been deposited on the spokes,
(d) a detector positioned so that the spokes pass sequentially through it after passage through the evaporator(s),
(e) one or more coolers, positioned so that the spokes pass through it or them after passage through the detector,
(f) a stepper motor adapted to move the spokes in a series of discrete steps, and
(g) a control system for the stepper motor, evaporators and coolers.

The system is particularly suitable for use in HPLC analysis and may be interfaced with a plasma spectrometer.

8 Claims, 2 Drawing Sheets

TRANSPORT DETECTOR SYSTEM

This invention relates to a novel transport detector system suitable for use with high performance liquid chromatography (HPLC).

High performance liquid chromatography is one of the most widely used techniques in analytical chemistry. Its purpose is to separate a mixture of materials by passing a solution of the mixture through a chromatographic column so designed that the separated components of the mixture elute from the column at different times. The separated components may be detected and quantified individually. Detection and measurement is generally achieved by monitoring the uv absorbance of the eluate at a predetermined wavelength, although a number of alternative techniques may be used for components with particular properties.

Some compounds show no strong uv absorbances at any readily accessible wavelength—indeed some compounds have no specific properties which can readily be used for a chromatographic detection process. For example, alkanes have no uv absorbance above 200 mm, no specific electrochemical characteristics, and no strong fluorescence emission. Such compounds are difficult to detect with high sensitivity in the liquid phase.

In the related separation technique of gas chromatography several highly sensitive detector systems are available. One of these is the flame ionisation detector (FID), in which components eluting from the chromatographic column in an inert carrier gas are burned in a hydrogen-oxygen or hydrogen-air flame, and ions released during the combustion are detected electronically. This approach is suitable for the detection of most carbon containing compounds, producing a detection signal which is closely related to the number of carbon atoms passing through the detector. The principal difficulty in utilising this technique for liquid chromatography is that the majority of the liquid eluents appropriate for use in HPLC contain carbon atoms, and consequently give rise to a large "background" signal if passed directly into an FID.

An FID may be incorporated into a liquid chromatography detection system if the carbon containing solvent is removed from the column eluate before the latter is combusted in the FID, but this has not been easy to achieve.

A previous attempt at solving this problem involves the use of a continuously moving wire. The wire is passed through the eluate and some of the latter is retained on its surface as a coating. Solvent is evaporated by passing the wire through a low temperature oven and the residual components are then volatilised and combusted in a high temperature oven. The resulting carbon dioxide is then hydrogenated to methane and the methane passed into the FID for recombustion. Before coating, the wire is generally cleaned in a high temperature oven.

Although the moving wire is generally satisfactory and fulfils a useful role, it suffers from a number of disadvantages:

(1) Since the wire is continuously moving and is of small diameter, it is difficult, if not impossible, to pick up all the eluate, thus reducing the sensitivity of the detector.
(2) For the same reason, the quantity of eluate retained by the wire is dependent upon the viscosity of the eluent.
(3) The wire itself is required to withstand the high temperaures used in the volatilisation/combustion and cleaning stages, which are sometimes higher than the wire can tolerate without distortion or damage.
(4) The wire is a good conductor of heat, thus making the maintenance of distinct regions of high and low temperatures difficult.
(5) The wire requires mechanical support with inherent problems of contamination of the support materials and the consequent recontamination of the wire.
(6) Because the eluate coating is directly exposed to high temperatures, boiling occurs with the risk of sputtering and loss of sample from the wire.

We have now designed a novel transport detector system, particularly suitable for HPLC, but not restricted thereto, which does not suffer from the above disadvantages and which is particularly suitable for control by a computer.

Thus according to the present invention there is provided a transport detector system comprising
 (a) means for supplying liquid,
 (b) a plurality of moveable spokes, the spokes being positioned to pass in sequence across the liquid supply means whereby liquid is deposited on the spokes, the spokes being constructed from a refractory inorganic material of low thermal conductivity,
 (c) one or more evaporators, positioned so that the spokes pass sequentially through it or them after liquid has been deposited on the spokes,
 (d) a detector positioned so that the spokes pass sequentially through it after passage through the evaporator(s),
 (e) one or more coolers, positioned so that the spokes pass through it or them after passage through the detector,
 (f) a stepper motor adapted to move the spokes in a series of discrete steps, and
 (g) a control system for the stepper motor, evaporators and coolers.

The means for supplying liquid may be a delivery tube, which may be heated. This may be achieved by providing an inner tube for the passage of liquid and an outer tube surrounded by a heating element. The delivery tube may additionally be fitted with a transfer wire which brushes against the spokes to ensure efficient transfer of liquid. The liquid will generally be transferred at a rate in the range 0.01 ml/min to 20 ml/min.

The system may contain an evaporator located at the point where eluate is delivered to a spoke. This combines with the delivery tube heater to assist in the evaporation of solvent as rapidly as possible after it leaves the delivery tube.

The spokes are preferably silica rods, most preferably about 1 mm in diameter. Other refractory materials such as sapphire may also be used. These materials can withstand the high temperatures involved, are mechanically robust and do not distort or expand to any significant exent. There is little thermal stress overall since each spoke accommodates its own, and there is no cumulative effect. The spokes rotate without directly touching any other part of the detector and therefore no seals are required. In addition, they are generally poor conductors of heat, and thus heat supplied is retained where it is needed and temperature control is readily achieved.

The liquid is preferably deposited on the spokes at or near their tips. In order to increase the surface area available for liquid adsorption, the tips may be expanded. In order to reduce the possibility of liquid flowing towards the centre, the spokes may be set at a slight upward angle from the tips.

The spokes may project radially outwards from a circular hub which is driven by the stepper motor.

Alternatively, the spokes may be mounted on a belt which passes around two wheels, one of which is driven by the stepper motor and thereby moves the belt, the planes of the spokes projecting outwardly at right angles to the belt. Although more complex, this system has the advantage that the distance between the spoke ends is variable, the spoke ends being closer together when on the straight sections of the belt between the two wheels and being further apart on the curved sections of the belt passing over the wheels. Thus it is possible to arrange for a small separation of the ends in the vicinity of the evaporators and coolers by positioning the latter alongside the straight sections of the belt and a greater separation of the ends in the vicinity of the detector by placing it alongside one of the wheels.

As stated above, the transport detector is particularly suitable for use in HPLC analysis. When this is the case, the liquid supplied to the spokes will be eluate comprising a relatively volatile solvent and relatively involatile solute. The solvent may be a mixture of liquids of differeing volatility. When this is so, it will be advantageous to use a number of evaporators operated under different temperature conditions to ensure progressive and smooth evaporation of the solvent, leaving behind the less volatile sample components. This avoids the violent boiling which can occur when only one evaporator is used and the lowest boiling component of the solvent is exposed to the temperature necessary to volatilise the highest.

Suitable evaporators are formed by hot air blowers. Generally a range of three, including one associated with the delivery tube, each designed to accommodate one or more spokes and operating at temperatures between 20° C. and 300° C. will be sufficient. Each evaporation stage has a separately defined operating temperature and air flow rate, parameters which may be optimised for specific sample types and eluent flow rates.

Suitable detectors include flame ionisation detectors, flame photometric detectors and nitrogen/phosphorus detectors. Between them, these possess universal detection capability with the possibility of carrying out selective detection for sulphur (e.g. in petroleum products), nitrogen (also in petroleum products and in amino acids, peptides, proteins, dyes, drugs, etc) and phosphorus (e.g. in pesticides and petroleum additives).

When a spoke passes into the flame of an FID, the hot flame volatilises and combusts the residue on the spoke, giving an FID signal which is recorded. Because the spokes are made of a non-conducting material, only the ends of the spokes reach the high temperature associated with the FID flame, but this is usually adequate to ensure that the spoke is cleaned of residue and so available for reuse.

If not, however, a clean-up flame can be incorporated after the FID. This may be desirable for certain types of compounds which are not cleanly and completely combusted in the FID, e.g. sugars, which tend to char, and heavy petroleum residues, such as asphalts and bitumens, which tend to produce refractory cokes.

The coolers are provided to reduce the spoke temperature before the deposition of further eluent. Suitable coolers are formed by air fans. Again, for ease of control, more than one is desirable. Two, each designed to accommodate three to five spokes simultaneously, will generally be sufficient. Control is achieved by controlling the rate of air flow.

The stepper motor may advance the spokes at any desired rate. Generally a rate within the range 4 steps per second to 1 step per 10 seconds will be suitable.

It is important to appreciate that the stepper motor does not rotate at a fixed velocity. The stepper motor moves in a series of discrete steps and the time taken to move a spoke through one step is short compared with the time that the motor remains motionless with one spoke receiving eluate, several spokes waiting in the evaporating and cooling air flows and one spoke being treated in the FID. Stepping is under control, preferably computer control, and the stepping rate is one of the parameters which may be optimised to handle a specific sample type and eluate flow rate.

Stepping has a number of advantages over continuous movement.

(1) It is more amenable to control, particularly computer control,
(2) The residence time in the various stages may be selected so that the desired operation has time to be effected,
(3) Detection takes place only when a spoke is in the vicinity of the detector so that the signal from the detector is also given in a series of steps, which is easier to interpret,
(4) The subsequent cleaning of the spokes is more easily achieved.

Suitable stepping motors are commercially available.

Because of the large numbers of variables employed, e.g., eluate flow rates, evaporator flow rates and temperatures, cooler flow rates and rate of stepping, an effective control system is required. This is best achieved by a suitably programmed microcomputer through a multifunction interface system.

The system may incorporate a self-monitoring feedback and control loop. If the signal from the detector is unexpectedly high, probably representing incomplete evaporatiion of the solvent, the control system can be programmed to take remedial action, for example by increasing the temperature and/or flow rates from the evaporators. The system may be used as an on-line monitoring and/or control instrument.

The system is suitable for use with a conventional HPLC chromatographic column using a hydrocarbon solvent and is thus particularly suitable for type analysis of hydrocarbons boiling in the range 300° C. and upwards.

However, because of the flexibility of the detector it is possible to extend the applicability of HPLC to other systems including lower boiling hydrocarbons. Other potential applications include the analysis of pharmaceuticals such as alkaloids, antibiotics, steroids and analgesics; of biochemical compounds such as aminoacids, peptides, proteins, carbohydrates, lipids and vitamins; of industrial chemicals such as pesticides, petroleum products, petrochemicals, polymers and dyestuffs; and of environmentally hazardous compounds such as polycyclic aromatics and chlorinated hydrocarbons.

The eluent need not be limited to hydrocarbons and hydrocarbon mixtures. Other substances such as water and alcohols may also be employed.

The transport detector system can also act as an interface for sample introduction into spectrometers for elemental analysis, either from an HPLC column or from some other source. Suitable spectrometers include mass spectrometers, pyrolysis mass spectrometers, spectrophotometers and plasma spectrometers.

Suitable plasma spectrometers are: Inductively Coupled Plasma Atomic Emission Spectrometers (ICPAES), ICP Mass Spectrometers (ICP-MS), and Microwave Induced Plasma Atomic Emission Spectrometers (MIPAES). The invention is particularly applicable for:

(a) use of the above spectrometers as element specific detectors for high performance liquid chromatography (HPLC),
(b) as an autosampler for element analysis of small (10 μl) samples using these spectrometers.

In ICPAES, the sample is normally in the form of a solution. This solution is usually introduced into the plasma (normally argon gas), through a pneumatic nebuliser and spray chamber. This allows about 2-3% of the solution (as a fine mist in argon gas), to pass into the plasma. In the plasma (temperature 8000°–1000° K.), the solution droplets are dried, the sample molecules are dissociated and the atoms are excited into higher atomic and ionic states. As these atoms and ions relax to their respective ground states, characteristics lines are emitted in the visible and uv regions of the spectrum, whose intensities are related to the concentrations of the elements in the original sample. The intensities of these lines are usually measured using a conventional monochromator or polychromator, (although Fourier Transform instruments are also now becoming available).

The plasma source in ICP-MS is essentially identical to that used in ICPAES. However, rather than observing the optical emission from the plasma, the ions are extracted into a quadrupole mass spectrometer. The advantages over ICPAES are:

(i) Detection limits are typically 2 orders of magnitude lower
(ii) All elements are detected almost simultaneously, (the complete mass range can be scanned in about 30 ms)
(iii) Isotopic ratios can be measured, (useful for tracer studies)

The MIP (usually He) can be used as a source for atomic emission spectrometry. The principle advantage over the argon ICP is that emission can be observed for non-metals such as hydrogen, carbon and the halogens which are difficult or impossible to excite using the latter technique. The principal disadvantage however, is that the MIP is extremely intolerant of solvents, necessitating that samples are desolvated prior to introduction into the plasma.

In most previous attempts at interfacing an HPLC column with a plasma sepctrometer, the effluent from the column has been introduced to the plasma using a conventional pneumatic nebuliser and spray chamber. This has several disadvantages:

(i) Transport efficiency is only about 2-3% and so sensitivity is lost.
(ii) Volatile solvents extinguish the plasma.
(iii) Increased dispersion in the spray chamber gives rise to broadening of the chromatographic peaks.

The problems associated with the first two of these problems can be reduced to a certain extent using desolvation systems on the spray chamber but this has the effect of making the third problem worse.

As previously stated, the transport system hereinbefore described is particularly suitable for interfacing with a plasma spectrometer.

Thus according to a further feature of the present invention there is provided a transport detector system wherein the detector is a hydrogen flame, the system comprising (a) means for supplying liquid,
(b) a plurality of moveable spokes, the spokes being positioned to pass in sequence across the liquid supply means whereby liquid is deposited on the spokes, the spokes being constructed from a refractory inorganic material of low thermal conductivity,
(c) one or more evaporators, positioned so that the spokes pass sequentially through it or them after liquid has been deposited on the spokes,
(d) a hydrogen flame, positioned so that the spokes pass sequentially through it after passage through the evaporator(s),
(e) one or more coolers, positioned so that the spokes pass through it or them after passage through the detector,
(f) a stepper motor adapted to move the spokes in a series of discrete steps,
(g) a control system for the stepper motor, evaporators and coolers, and
(h) a plasma spectrometer adapted to receive combustion products from the hydrogen flame.

The hydrogen flame is a modification of the FID hereinbefore described. Air is supplied to the hydrogen flame via a concentric tube. When a spoke passes into the flame, the hot flame volatilises and combusts the residue on the spoke. The combustion products are swept into the plasma by a flow of helium or argon from below the flame. Once in the plasma, the analyte is atomised, ionised and excited into higher atomic and ionic states. Analysis is carried out using a conventional optical or mass spectrometer in the usual manner.

An optional suction unit can be placed between the hydrogen flame and the plasma. This provides suction to draw up the combustion products by the venturi effect and provides additional pressure to punch through the fireball of the plasma.

The transport detector system interfaced with a plasma spectrometer has the following advantages:

(i) Transport efficiency close to 100%.
(ii) Minimum broadening of chromatographic peaks.
(iii) Can be used with any common solvent, with flow rates in the range 0.01 ml/min to 20 ml/min.
(iv) Can allow simultaneous multi-element determinations to be carried out.
(v) Gives increased freedom from matrix effects.
(vi) Allows introduction of analyte to the plasma without accompanying solvent, thus allowing use of an MIP and reducing spectral interference problems in ICP-MS.
(vii) Is applicable to most elements in the periodic table (including non-metals such as hydrogen, carbon and the halogens).

As an alternative to depositing eluate from a chromatographic column on the spokes, small samples for elemental analysis (10 μl), may be pipetted onto the spokes. This approach has two principal advantages:

(i) Elemental analysis can be carried out on extremely small samples
(ii) Analytes can be introduced to the plasma without accompanying solvent, giving rise to greater freedom from matrix effects and potentially increased sensitivity and allowing use of an MIP for determination of non-metals.

The conventional approach for this type of analysis has involved electrothermal vaporisation. However, this approach is very slow since no measurements can be made during the evaporation stage (normally about 60 seconds), or during the cooling stage (normally about 2 minutes), of the analytical cycle. The present approach is advantageous since measurements can be carried out using one spoke while another is cooling, a third is in the evaporation stage and sample is being introduced to a fourth. This should, therefore, greatly speed up the rate of analysis.

Figure 2:
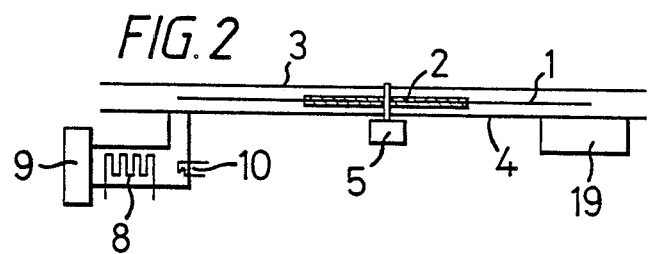
Figure 3:
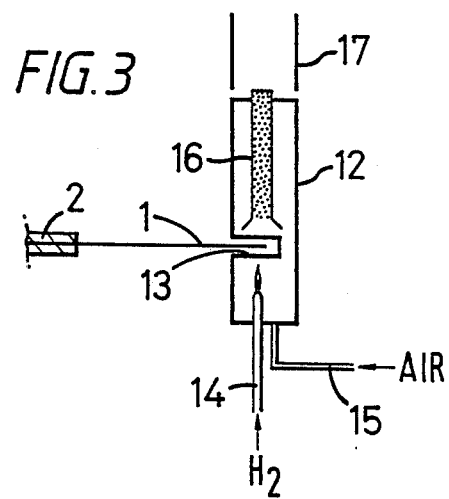
Figure 4:
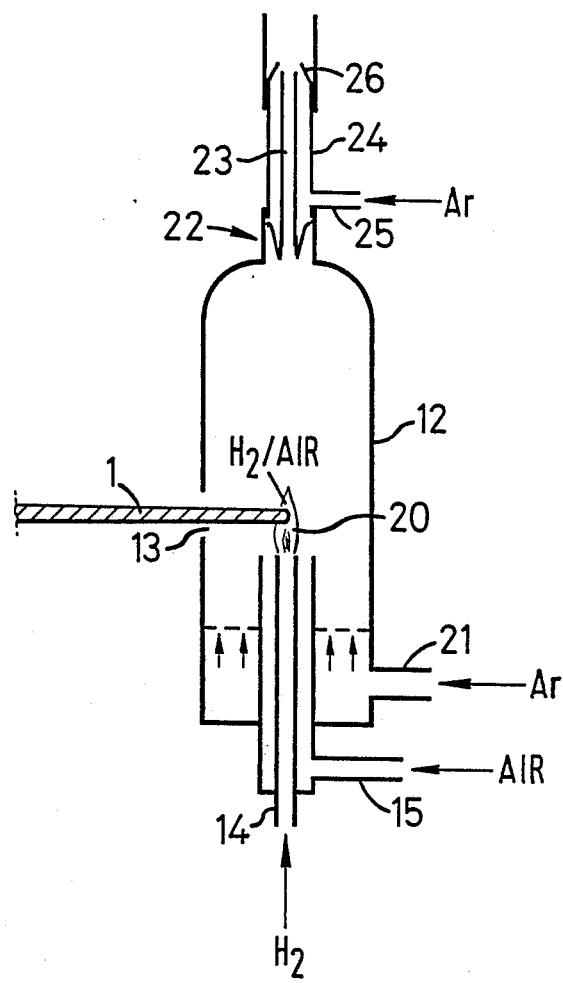

The transport detector system can also be used for other applications, either in one of the forms as hereinbefore described or with further minor modifications, e.g.,
(i) the cooled spokes may be effective in condensing and collecting certain components of gaseous mixtures,
(ii) the ends of the spokes may be coated with an adsorbent material and/or a selective membrane so that they will selectively adsorb desired compounds The invention is illustrated with reference to FIGS. 1 to 4 of the accompanying drawings wherein
FIG. 1 is a plan view of the transport detector system,
FIG. 2 is a sectional elevation,
FIG. 3 is a detail showing the detector and
FIG. 4 is a diagram of a plasma spectrometer interface showing an optional suction unit.

The transport detector system is based on a number of quartz rods 1 mounted on a central hub 2 to form a spoked wheel. In the system shown, 32 rods are present, each approximately 1 mm in diameter and 12 cm long. The hub 2 is formed of two circular grooved aluminum discs and the rods 1 are sandwiched between them and maintained in position by rubber seals.

The wheel is positioned between a top baffle plate 3 and a lower base plate 4 which provide mechanical support for the system components. These plates also serve to provide the pathways for the evaporating and cooling air flows. The wheel is mounted directly on the shaft of a stepper motor 5 and is rotated in discrete steps.

During rotation, each spoke passes in turn beneath an eluate delivery tube 6 which deposits a drop of eluate on to its tip.

Typical quantities are 10 microliters per spoke with the spokes moving at 2 steps per second with an eluate flow rate of 1.2 ml/min.

Further rotation advances the spokes through a series of three evaporators 7 operated under different conditions of temperature and/or air flow which evaporates the solvent from the eluate leaving the solute behind. The first of these is positioned immediately adjacent to the delivery tube.

The evaporators consist essentially of a heating element 8, a fan 9 and a temperature sensor 10. The evaporating heaters are mounted below the base plate, blowing upwards through holes in both the base plate and the top plate.

After passing through the evaporators 7, the spokes pass into a modified FID 11 where the tips of the spokes are exposed to a hydrogen flame.

The FID comprises a body 12, a slot 13 for the spokes, inlets 14 and 15 for hydrogen and air respectively, a collector 16 and a chimney 17.

The FID is mounted in a slot cut in both the base and top plates and is positioned so that a spoke end lies directly above the flame jet 20 as shown in FIG. 3. The slot 13 is made only 1 mm larger than the spoke diameter to minimise the entry of extraneous gases and vapours into the flame region.

The heat of the hydrogen flame is sufficient to combust the residue on the spokes and leave them in a clean condition suitable for further deposition and analysis.

Before this, however, the spokes are cooled in a series of two coolers 18. The coolers are simply air fans 19 mounted below slots in the mounting plate 4.

The cooling fans are mounted directly on the base plate and the air draught from each fan covers approximately 4 spokes at any one time.

Above the top plate a number of partitions, not shown, maintain a separation between the warm air flow from the evaporator stages, the air flow from the cooling region and the region around the FID.

A microcomputer, not shown, controls the operation of the stepper motor, evaporators and coolers.

With reference to FIG. 4.

Items 1, 12, 13, 14 and 15 are as hereinbefore described,

When a spoke 1 passes into the hydrogen/air flame 20, the hot flame volatilises and combusts the residue on the spoke. The combustion products are swept into the plasma by a flow of helium or argon from below the flame supplied by a line 21.

The optional suction tube 22 can be placed between the hydrogen flame 20 and the plasma. This comprises a central tube 23 for the combustion products surround by a concentric ring 24 supplied with further quantities of helium or argon by line 25. Suction is provided by a venturi nozzle 26.

We claim:
1. A transport detector system comprising
    (a) means for supplying liquid,
    (b) a plurality of moveable spokes, the spokes being positioned to pass in sequence across the liquid supply means whereby liquid is deposited on the spokes, the spokes being constructed from a refractory inorganic material of low thermal conductivity,
    (c) one or more evaporators, positioned so that the spokes pass sequentially through it or them after liquid has been deposited on the spokes,
    (d) a detector positioned so that the spokes pass sequentially through it after passage through said one or more evaporators,
    (e) one or more coolers, positioned so that the spokes pass through it or them after passage through the detector, and
    (f) a stepper motor adapted to move the spokes in a series of discrete steps.
2. A system according to claim 1 wherein the detector is a flame ionization detector.
3. A transport detector system according to claim 1 wherein the detector is a hydrogen flame, and further comprising (h) a plasma spectrometer adapted to receive combustion products from the hydrogen flame.
4. A system according to claim 1 comprising an evaporator located at the point where eluate is delivered to a spoke.
5. A system according to claim 1 wherein the spokes are silica rods.
6. A system according to claim 1 wherein the spokes project radially outwards from a circular hub driven by the stepper motor.
7. A system according to claim 1 wherein the evaporators are hot air blowers.
8. A system according to claim 1 wherein the coolers are air fans.

* * * * *